US005455565A

United States Patent [19]
Moeenziai et al.

[11] Patent Number: 5,455,565
[45] Date of Patent: Oct. 3, 1995

[54] FLUID MONITOR SYSTEM AND METHOD USING A RESONATOR

[75] Inventors: Behzad Moeenziai, San Diego; Kurt Zublin, Poway; Jack Goldberg, San Diego, all of Calif.

[73] Assignee: IVAC Corporation, San Diego, Calif.

[21] Appl. No.: 149,184

[22] Filed: Nov. 8, 1993

[51] Int. Cl.⁶ ................................................ G08B 21/00
[52] U.S. Cl. ........................ 340/603; 340/632; 604/65
[58] Field of Search .......................... 340/603, 632;
331/65; 324/682, 636; 604/65; 73/861.95

[56] References Cited

U.S. PATENT DOCUMENTS

| | | | |
|---|---|---|---|
| 2,621,517 | 12/1952 | Sontheimer | 73/304 |
| 2,718,620 | 9/1955 | Howe | 324/61 |
| 2,992,391 | 7/1961 | Haynes | 324/61 |
| 3,263,167 | 10/1962 | Foster et al. | 324/682 |
| 3,515,987 | 6/1970 | Zurbrick et al. | 324/61 |
| 3,684,952 | 8/1972 | Lundstrom | 324/61 |
| 4,014,206 | 3/1977 | Taylor | 73/19 |
| 4,235,095 | 11/1980 | Liebermann | 73/19 |
| 4,344,293 | 8/1982 | Fujiwara et al. | 62/126 |
| 4,391,146 | 7/1983 | Grindheim | 324/682 |
| 4,565,500 | 1/1986 | Jeensalute et al. | 340/632 |
| 4,599,888 | 7/1986 | Hufton et al. | 73/19 |
| 4,731,556 | 3/1988 | Adams | 310/338 |
| 4,751,476 | 6/1988 | Meijer | 331/65 |
| 4,938,079 | 7/1990 | Goldberg | 73/861.95 |
| 5,017,879 | 5/1991 | Lucas et al. | 324/663 |
| 5,073,167 | 12/1991 | Carr et al. | 604/114 |
| 5,091,704 | 2/1992 | Kopera | 331/65 |
| 5,198,777 | 3/1993 | Masuda et al. | 324/682 |
| 5,260,665 | 11/1993 | Goldberg et al. | 324/636 |

*Primary Examiner*—Jeffery A. Hofsass
*Assistant Examiner*—Julie Lieu
*Attorney, Agent, or Firm*—Fulwider, Patton, Lee & Utecht

[57] ABSTRACT

A non-invasive, fluid monitor engages an open resonator with a segment of fluid line. The fluid line is disposed such that it and the fluid within become a part of the dielectric loading on the resonator. The open resonator is a part of an oscillator circuit that changes frequency of oscillation in response to the dielectric loading on the resonator. A frequency discriminator monitors the frequency of the oscillator to detect an air bubble in the fluid line. In the case where the resonator comprises a microstrip line, the microstrip line is disposed in parallel to the segment of the fluid line and the length of the microstrip line is selected to be equal to or greater than the maximum length of air bubble permitted thus providing a volumetric air-in-line sensor. The output of the frequency discriminator is compared to a threshold to determine a frequency shift large enough to indicate the presence of an air bubble.

27 Claims, 6 Drawing Sheets

FLUID MONITOR SYSTEM AND METHOD USING A RESONATOR

BACKGROUND

The invention relates generally to monitoring fluid in a line without direct fluid contact, and more particularly, relates to non-intrusively monitoring for the presence of air in that fluid.

In numerous medical and industrial applications, continuous in-line monitoring of a fluid is often necessary to ensure consistency of a process or to ensure safety. For example, the presence of air within a fluid may need to be monitored for various reasons. Examples of non-medical applications for fluid monitoring without direct fluid contact can be found in the chemical process industry, where inexpensive and/or disposable fluid conduits may be required, where fluids may be present at high pressure, or where fluids that are highly caustic or highly toxic may be involved.

In the medical area, safety and cost are of great concern. Reliable and inexpensive in-line fluid monitoring without direct fluid contact is especially important in the medical area where sterilization is required and disposability of the fluid line is desired. One particularly important purpose of in-line fluid monitoring is the detection of air. Air-in-line detection systems are used to prevent the inadvertent infusion of a dangerous quantity of air into a patient's bloodstream. While small bubbles of air may have no adverse effect on a patient, large air bubbles can cause death. The amount of air that is dangerous can vary and depends on patient characteristics; therefore, the ability to detect various sizes of air bubbles is desirable.

Methods and systems for the in-line detection of air have typically involved ultrasound or light transmission through the fluid line being monitored. The transmission characteristics of sound or light may be utilized as an indication of the presence of a gas bubble in liquid in the fluid line. Simple recognizable perturbations of the signals from such sensors may be utilized to trigger an alarm and/or halt the infusion. Such systems require that the fluid and the associated conduit be substantially transparent to the energy being transmitted. However, in some cases the detection system is unable to reliably distinguish between air bubbles of varying sizes, resulting in erratic behavior with false indications of the presence of air bubbles. Typically, such detection systems do not accurately determine the exact size of air bubbles and are configured merely to indicate the presence of air bubbles that are greater than a predetermined size.

In optical systems, extraneous light reaching the optical detector can compromise the system's accuracy. In acoustic frequency systems, good mechanical coupling of the transducers to the fluid line is of large importance. Poor mechanical coupling will mask from the detection system the case where the air detected is located between a transducer and the fluid line rather than actually within the fluid line. Consequently, the false alarm rate may be unacceptably high. As a result of this consideration, much effort and expense have gone into the mechanical design of the detection system coupler to obtain good mechanical coupling. Such systems may occasionally still have less than desirable mechanical coupling where the fluid line sizes vary or foreign materials become stuck to the outside of the fluid conduit and come into contact with the coupler.

A further consideration in air-in-line detections systems is the determination of the exact volume of the air bubble in the fluid line in which fluid is moving. Many systems use transducers that are smaller than the volume of air in the fluid conduit that would pose a danger to the patient. Some such systems "time the bubble." That is, once a quantity of air is detected, a timer is initiated to determine the amount of time that the detector "sees" the air. A processor then calculates the bubble size based on the internal volume referenced to the transducer size, the flow rate, and the time the bubble is detected. Processing is made more complex in the case where a train of bubbles exists where the bubbles are interspaced with liquid and the transducers alternately indicate air and liquid. Such processing can result in a large increase in expense and complexity.

Other apparatus capable of detecting impurities such as air within a fluid include electrochemical systems and laser doppler systems. Electrochemical systems can be extremely sensitive to specific compositional variations in a fluid, but incorporate components, such as membranes, that must be in direct contact with the fluid, thus increasing their costs in applications requiring disposability. Laser systems are at present very expensive, and still other systems cannot operate over the wide range of flow rates and fluid types required in many applications.

Hence those concerned with fluid line monitoring have recognized that it would be beneficial to provide an in-line fluid monitoring system and method that do not involve direct fluid contact with a sensor but that exhibit higher sensitivity to variations in fluid composition, including the presence of air and that can provide an indication of the size of an air bubble. In medical systems, there is a need for an apparatus and a method that reliably and accurately detect and quantify the presence of air in the line but at the same time are relatively inexpensive and can function with an inexpensive disposable fluid line. The present invention fulfills these needs and others.

SUMMARY OF THE INVENTION

Briefly and in general terms, the present invention involves a new and improved system and method for fluid monitoring without direct fluid contact. Detection of fluid properties, including the presence of air is provided. The system and method in accordance with the invention include the use of an open resonator having a selected characteristic that changes in response to a selected substance sought to be detected in a container. A circuit is coupled to the open resonator and is responsive to the selected characteristic of the open resonator and provides an output signal that varies in dependence on the characteristic of the open resonator. The container is disposed at a position in relation to the open resonator such that the existence of the selected substance in the container will change the characteristic of the open resonator. A processor receives the output signal of the circuit and monitors that signal to detect the presence of the selected substance in the container.

In a more detailed aspect of the invention, the circuit is frequency dependent on the characteristic of the open resonator and the output signal of the circuit is responsive to that frequency. In another aspect, the, selected characteristic of the open resonator is its impedance and the impedance changes in response to the existence of the selected substance in the container. The circuit is dependent on the impedance of the open resonator and the: output signal of the circuit is responsive to that impedance.

A further aspect involves locating the container in a fringe electric field of the ,, open resonator to affect the selected characteristic of the resonator.

In yet a further aspect, the container is positioned in a main electric field of the open resonator to affect the selected characteristic of the resonator.

In a more detailed aspect, the container is positioned so that the particular entire fringe or main electric field includes at least a part of the container.

In a further detailed aspect, the resonator comprises a microstrip stub that forms a part of an oscillator circuit and affects the frequency of oscillation of the oscillator. The frequency of oscillation is monitored by another circuit and that frequency is used to determine the contents of a fluid line. Changes in that frequency of oscillation are used to detect the presence of air in the fluid line.

In a further detailed aspect, the microstrip stub is disposed so that its entire length is loaded by the fluid line segment. The microstrip segment is disposed in a parallel configuration to the fluid line segment.

A processor is used to compare changes in the oscillating frequency to predetermined parameters to detect the presence of an unacceptable amount of air in the fluid line. A look-up table may be provided in a memory device accessed by the processor so that certain changes in the oscillating frequency may be correlated with the volume of air in the fluid line segment and such changes indicated to the user. For example, an inhomogeneity such as an air bubble presents a markedly different dielectric load than pure liquid in the fluid line segment and thus its presence in the fluid line segment is accompanied by a large shift in the oscillating frequency.

Other aspects and advantages of the invention will become apparent from the following detailed description and the accompanying drawings, illustrating by way of example the features of the invention.

DETAILED DESCRIPTION OF THE PREFERRED EMBODIMENTS

Figure 1:
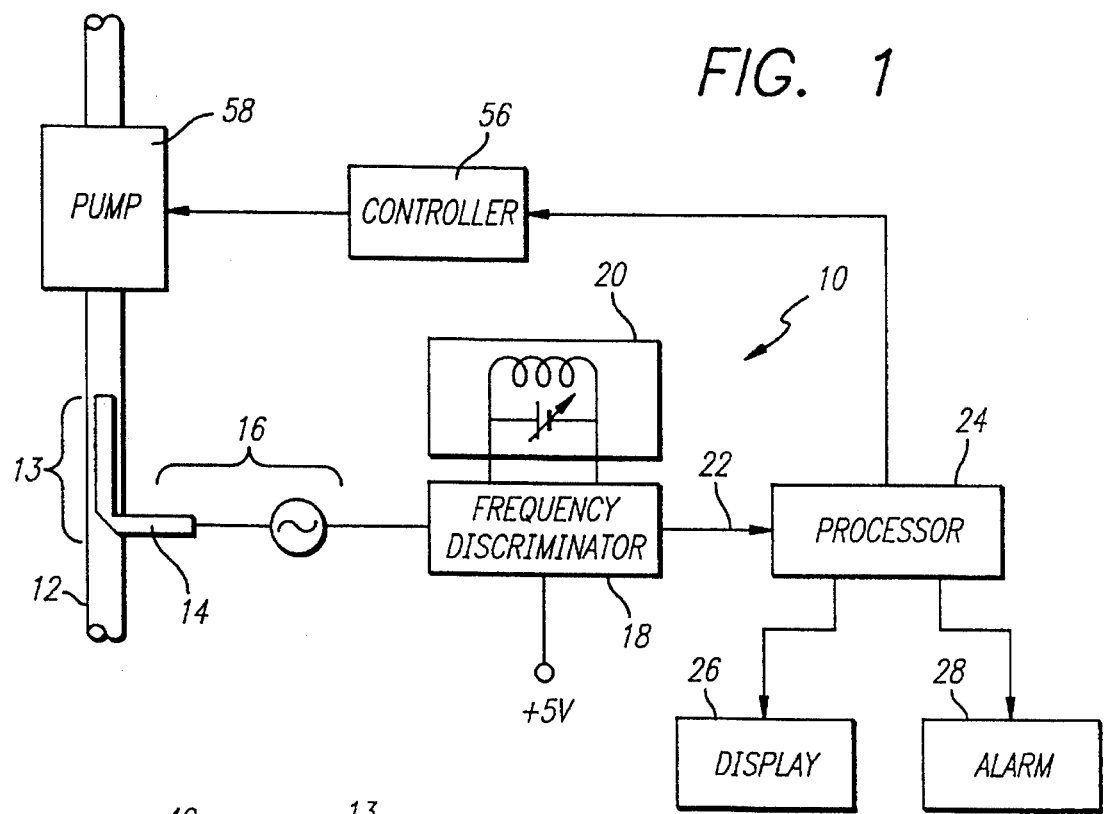
FIG. 1 is a diagram of a volumetric air-in-line sensor system having a microstrip stub shown engaged with a flexible fluid line such that the fluid line forms a part of the microstrip's dielectric loading.

Referring now to the drawings with more particularity, wherein like reference numerals designate like or corresponding elements among the several views, there is shown in FIG. 1 an air-in-line detection system 10 operating on a fluid conduit 12 through which fluid is flowing. Engaged with a segment 13 of the fluid line 12 is an open resonator that in this case is a microstrip line 14 having a selected length, width, and thickness. The microstrip line 14 is placed in parallel with the fluid line segment 13 and is open ended thereby forming a planar open resonator producing a standing wave. The microstrip line 14 forms a part of an oscillator 16, the frequency of oscillation of which depends on the impedance of the microstrip resonator 14. A frequency discriminator 18 having a tuned circuit 20 monitors the frequency of oscillation of the oscillator 16 and provides a voltage output 22 representative of that frequency. The voltage output 22 is compared by a processor 24 to a reference to determine if air is present in the fluid line 12 in an unacceptable quantity. The processor 24 may continuously display 26 the amount of air detected or merely present an alarm 28 in the event that air above the threshold is detected, or both. The alarm 28 may be audible or visual or both.

As shown in FIG. 1, a planar, open microstrip 14 or microstrip "stub" is employed. In accordance with an aspect of the invention, the microstrip stub 14 is made a part of the oscillator 16 circuit such that the dielectric loading on the stub 14 will affect the frequency of oscillation of the oscillator 16. As is well known to those skilled in the art, the dielectric loading on the stub will cause it to have a particular resonant frequency. In accordance with the invention, the fluid line and its contents are placed within an electromagnetic field created by the stub 14 so as to affect the dielectric loading on the stub 14 and thereby affect its impedance as seen by the oscillator 16. Any changes in the dielectric loading on the stub 14 caused by a change in fluid composition or the presence of air or other gas will therefore perturb the resonant characteristics and affect the frequency of oscillation of the oscillator 16 in an identifiable manner. In this case, the fluid line segment 13 is placed in the electric field of the stub 14.

Figure 2:
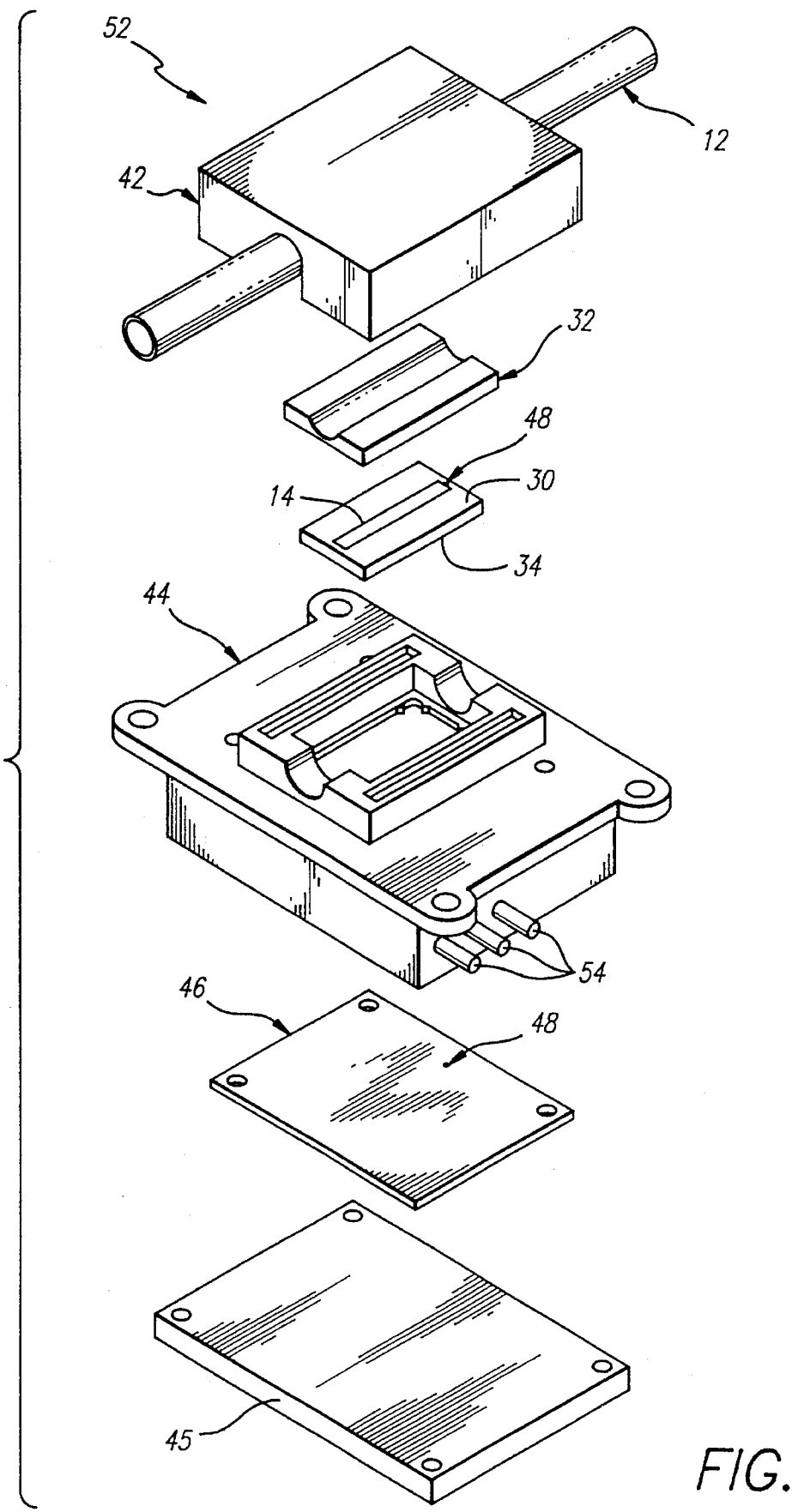
FIG. 2 is an exploded assembly drawing of an air-in-line detection system in accordance with the principles of the invention in which a planar microstrip stub is used as an open resonator.

Referring now to FIG. 2, placement of the fluid line 12 in the electric field of the stub 14 is shown. The stub 14 is mounted on a substrate 30 and a mounting structure 32 is placed above the stub 14 for cradling and properly positioning the fluid line. A ground plane 34 is located under the substrate 30 on which the stub is disposed. Another mounting structure (not shown) similar to the structure 32 is placed in contact with the tubing also to cradle and properly position the tubing and is located inside the housing cover 42 opposite the first mounting structure 32. Because the housing cover 42 is electrically conductive, it acts as another ground plane to the stub 14. In one embodiment, the housing cover 42 may be formed of a metallized plastic. The fluid line 12. is therefore located in a main electric field of the stub 14. It should be noted that the electric field created by the entire length of the stub 14 is affected by the fluid tubing 12 and its contents. Thus, the tubing and its contents will have a larger effect than if the tubing were placed in only a portion of the stub's electric field.

Figure 3:
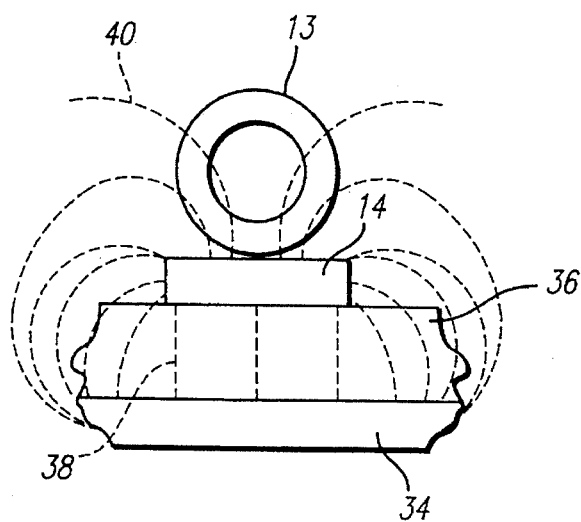
FIG. 3 is a partial end-on view of a fluid tubing placed over a microstrip stub with the fluid tubing located in the fringe field of the microstrip stub.

This effect is shown in further detail in FIG. 3. The microstrip stub 14 is mounted on a dielectric substrate 36 and a ground plane 34 is mounted on the opposite side of the substrate 36. The dielectric substrate 36 has a predetermined dielectric constant and may be formed of various materials known to those skilled in the art. In one embodiment, the substrate was selected of a material having low loss, uniform dielectric properties, close tolerances, and good temperature stability. Substrates from the Rogers Corporation known as Duroid™ have been used, although other materials are usable.

In FIG. 3, the main electric field 38 does not intercept the fluid conduit segment 13 while the fringe field 40 does. Although the fringe field is not as strong as the main field, it does contribute to the dielectric loading of the stub 14 and will have an effect on the impedance presented by the stub 14 to the oscillator 16 (FIG. 1). In addition, other resonant characteristics such as bandwidth and Q as well as the impedance of the stub 14 can be affected by dielectric loading. The captured segment 13 of the fluid line and the fluid therein form a part of the ambient dielectric medium and changes occurring in that fluid line and fluid will affect the dielectric properties of the medium. Thus, changes in the fluid composition such as the existence of air in the fluid will alter the dielectric loading and cause a consequent change in the resonant characteristics of the stub 14. By monitoring the stub's resonant characteristics, air in the fluid can be detected.

Although the tubing 13 is shown as being positioned directly over the microstrip line 14 in FIG. 3, it may be located at other positions within the fringe field 40. For example, the tubing may be located at the right side of the dielectric substrate 36 such that it is in the fringe field 40. Such a configuration may be easier to construct than that shown in FIG. 3.

Figure 4:
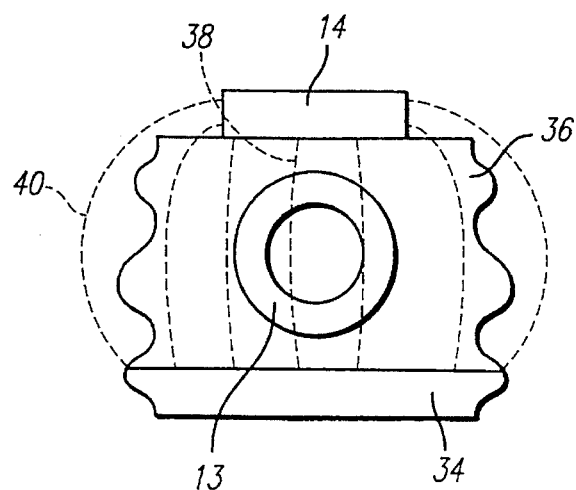
FIG. 4 is another partial end-on view of a microstrip stub with the fluid tubing positioned within the dielectric substrate between the microstrip and its ground plane thereby disposing the fluid tubing in the main electric field of the microstrip stub.

Another embodiment is shown in: FIG. 4 where the fluid line segment 13 is embedded in the dielectric substrate 36 and intercepts the main electric field 38 of the microstrip stub 14 to the copper ground plane 34. Typically, the main field has more concentration than the fringe field and this results in more sensitivity. Although such an arrangement may have mote of an effect on the impedance presented by the stub 14 to the oscillator 16, this arrangement may be more difficult to construct due to the requirement of embedding the fluid line 12 in a dielectric substrate 36.

Figure 5:
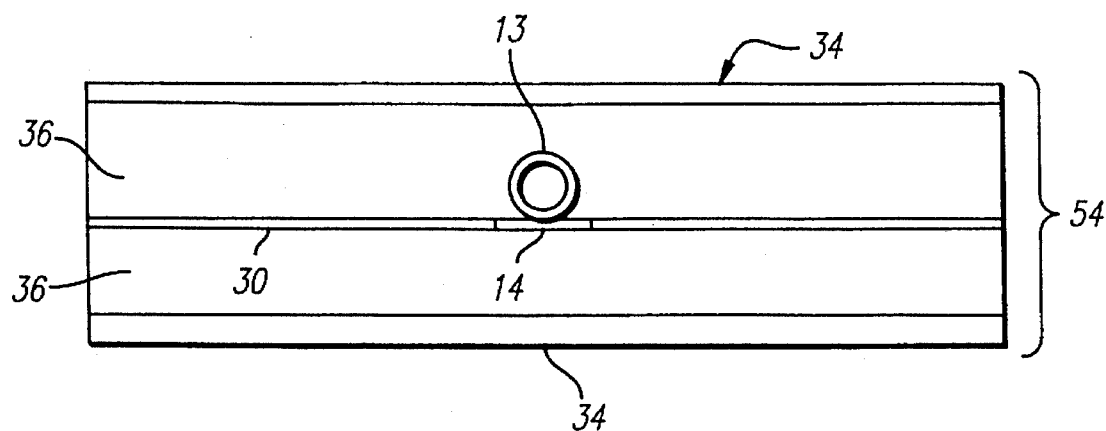
FIG. 5 is yet a further partial end-on view of a fluid tubing placed in a stripline structure such that it is located in a main electric field of the stripline.

Although FIGS. 3 and 4 illustrate unshielded or radiating microstrip resonators, a shielded configuration may be used in another embodiment. In FIG. 5, a modified stripline-type resonator 54 is illustrated. In this case, a resonant stripline element 14 is supported by the lower and upper substrates 36 which are both backed by ground planes 34. The fluid line segment 13 is disposed over the resonant element 14 at or near the region of maximum electric field and is sandwiched between the lower substrate 36 and the upper substrate 36. The two ground planes 34 together provide greater shielding than the microstrip structures of FIGS. 3 and 4. An appropriate channel must be cut into the upper substrate 36 to accommodate the fluid line segment 13. As the fluid line segment 13 is disposed such that it forms a major part of the dielectric loading of the resonator 14, changes in the composition of the fluid will perturb the structure's resonant characteristics. As in the other embodiments, the stripline 14 is oriented to be parallel to the fluid line segment 13 so that the fluid line segment 13 is disposed along the entire length of the stripline 14 for better coupling to its electric field. The configuration of FIG. 5 schematically more closely resembles the structure of FIG. 2 with ground planes and dielectric substrates on either side of the open stub.

The shielded approach, an example of which is illustrated in FIG. 5, is preferable in many applications because radiation from the open resonator 14 is controlled from reaching other circuits and external radiation from other circuits is inhibited from reaching the open resonator 14. The risk of false alarms caused by such external radiation reaching the open resonator 14 is lessened.

Referring again to FIG. 2, the tube housing cover 42 is located over the fluid line 12 to assist in properly locating the fluid line and provide a ground plane. The tube housing cover 42 may be formed of a metallic material and the mounting structures 32 (and the one inside the housing cover 42, not shown) may be formed of ABS plastic shaped to conform to the outside shape of the tubing 12. A sensor housing 44 is used for mounting all of the parts of the detector system except the processor 24, display 26, and alarm 28. The oscillator 16 and discriminator 18 with its tuned circuit 20 are mounted on the circuit board 46 mounted to the bottom of the sensor housing 44. Because the tube housing cover 42 is metallic and is in electrical contact with the sensor housing 44 that is also metallic, and the ground plane 34 of the stub 14 is in electrical contact with the sensor housing 44, an electrical path exists between the substrate ground plane 34 and the housing cover 42. Thus, the tube housing cover 42 acts as a second ground plane to the stub 14.

Locating holes 48 are formed in the stub 14, substrate 30, and in the circuit board 46 through which a conductor may be positioned to couple the stub 14 to the oscillator 16 located on the circuit board 46. Power, common, power monitor (described below), and discriminator output signals are coupled to and from the detector module 52 by means of RFI connecting posts 54 protruding from the side of the sensor housing 44. A bottom cover 45 that may also be formed of metallized plastic covers the bottom of the sensor housing 44.

In the case shown in FIG. 2, the dielectric constant of the substrate 30 on which the stub 14 is mounted may be selected to be close to or to equal the dielectric constants of the tubing mounting structures 32 (second one not shown) so that the main field is not concentrated only in the substrate 30 but also proceeds through the mounting structures and tubing 12 to the second ground plane formed by the tube housing cover 42 in sufficient concentration. In one embodiment, the dielectric constant of the ABS plastic used for the mounting structures 32 was approximately 3.0. The dielectric constant of the substrate 30 was selected to also be approximately 3.0. In other cases, the dielectric constant of the substrate 30 was allowed to vary between 2.2 and 6.0 with acceptable results still being obtained.

Figure 6:
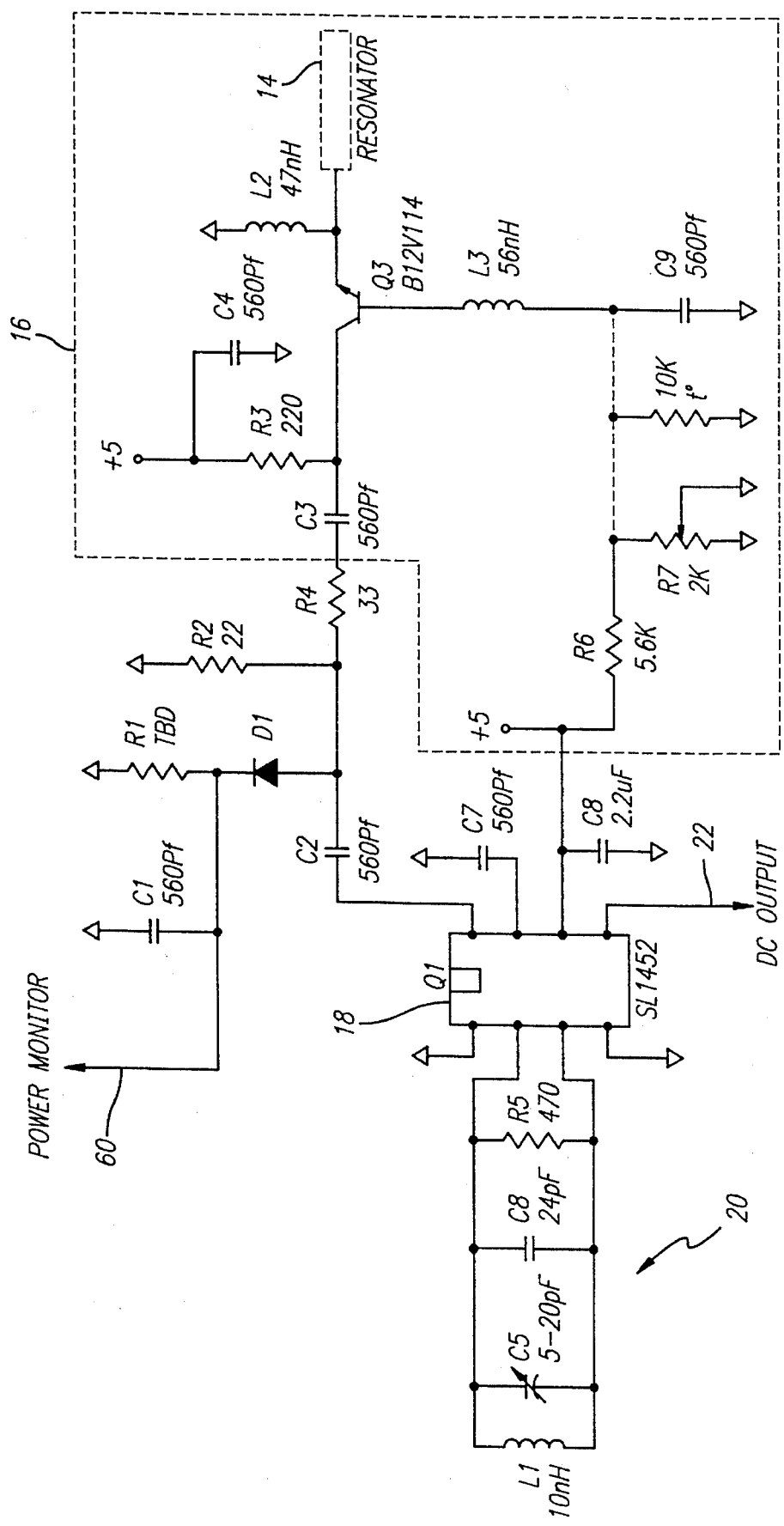
FIG. 6 is a circuit schematic diagram of a circuit that may be used to implement part of FIG. 1.

Referring now to FIG. 6, a circuit diagram is presented of an open resonator 14 coupled to a bipolar transistor oscillator 16, connected to a frequency discriminator 18 with its tuned circuit 20, and which provides the DC output signal 22 indicative of the frequency of oscillation of the oscillator 16. Those who are skilled in the art will recognize that the frequency of the oscillator 16 is affected by the resonant characteristics of the stub 14. Thus, changes in the dielectric loading of the stub 14 due to changes in fluid composition, including the presence of air or other gas, within the region of the electromagnetic fields of the stub 14 will result in a change in oscillation frequency.

Because the operation of the oscillator circuit will be apparent to those of ordinary skill, no further details are given here. However, the oscillator shown in FIG. 6 is not the only oscillator usable. Others may perform equally well. The circuit shown is used in this embodiment because it has been found to be dependable and achieves spontaneous oscillation under all conditions tested.

The power monitor output 60 of the circuit of FIG. 6 provides an indication of whether the circuit is operating. As long as the oscillator 16 is in an oscillating state, the power monitor output 60 will exist and indicate operation. However, if the oscillator 16 should cease oscillation, the power monitor output 60 would likewise cease and a fault alarm 28 may be given by the processor 24 (FIG. 1).

Figure 7:
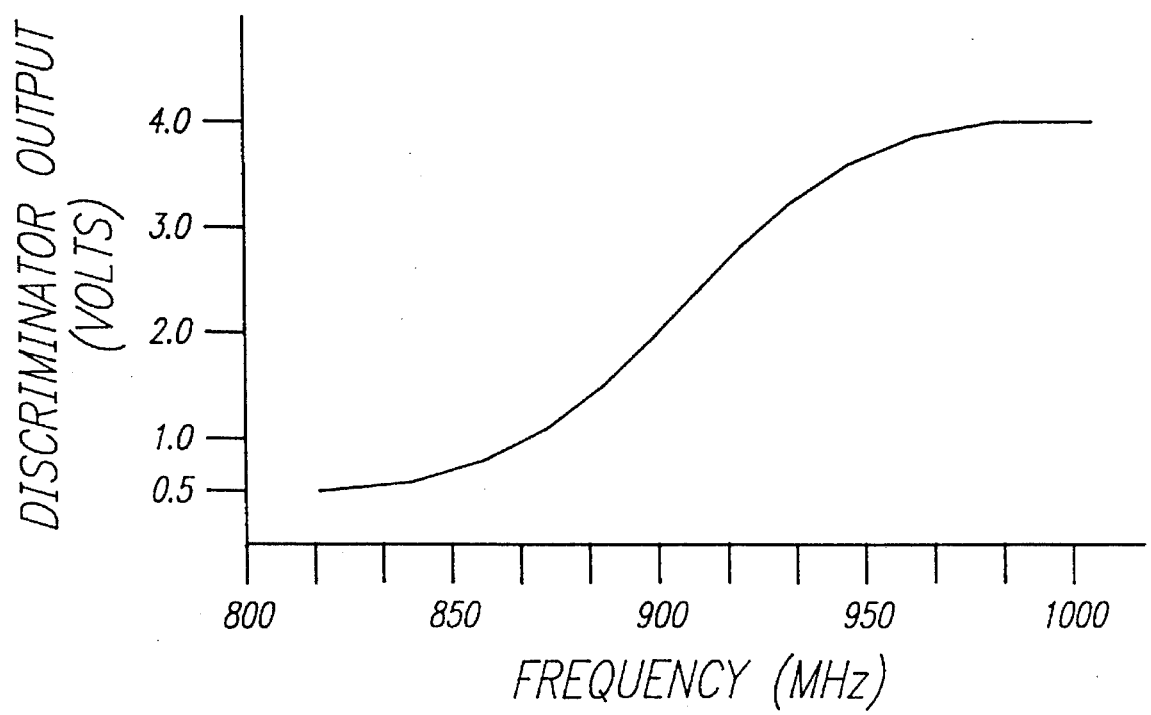
FIG. 7 is a graph of the variance of frequency discriminator voltage output responsive to the frequency of oscillation changes.

The oscillator of FIG. 6 is set to oscillate at 915 Mhz and the tuned circuit of the frequency discriminator is set to 915 Mhz. As is well known, the frequency discriminator 18 will output a DC voltage that varies in dependence on the frequency of the signal provided to its input. An example of the frequency discriminator output is presented in FIG. 7. As shown, the discriminator output varies with frequency as a typical "S" curve. The discriminator is adjusted to provide a linear output voltage for the maximum frequency excursion coinciding with the largest air bubble. The discriminator is "tuned" by the tuned circuit 20 to provide the linear output at a selected frequency. The variable capacitor C5 can be adjusted to achieve this linear output. In another embodiment, a variable capacitance diode (varactor) was used in place of the variable capacitor C5 to tune the circuit 20.

Figure 8:
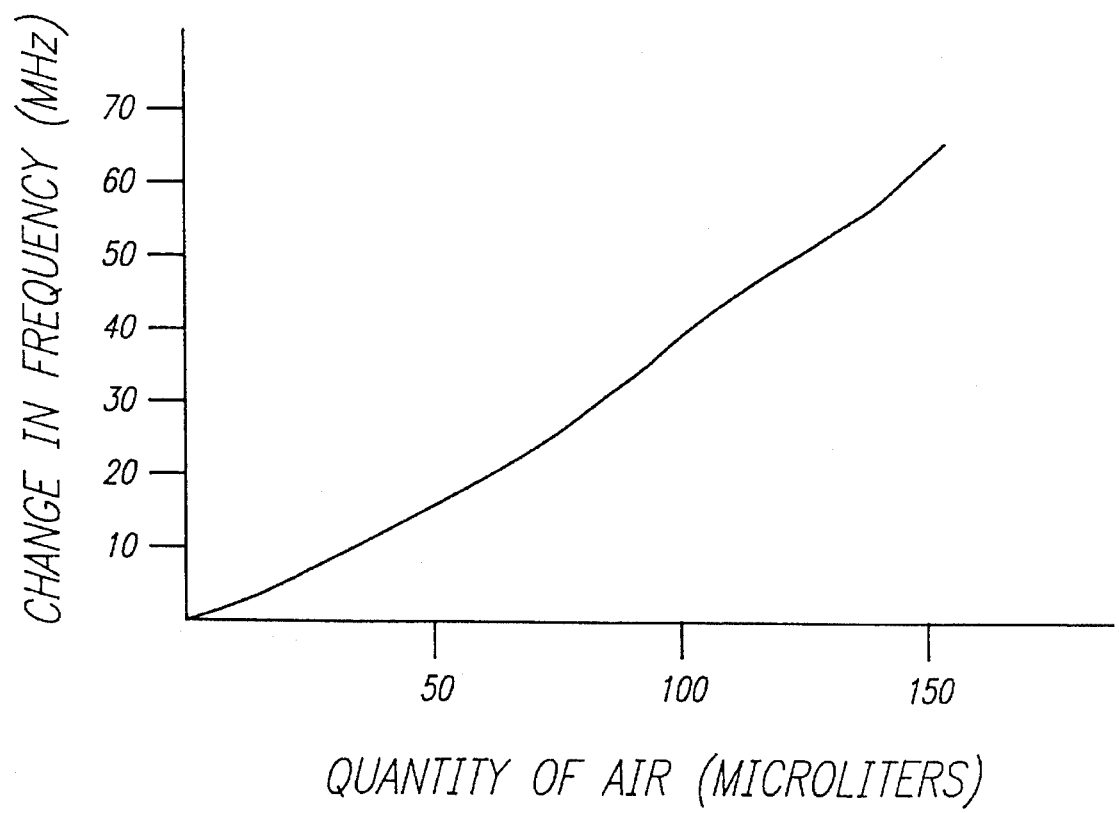
FIG. 8 is a sample graph illustrating the change in oscillating frequency in response to the detection of air in a fluid line.

Each fluid possesses particular dielectric properties. Gases, such as air, possess radically different dielectric properties than that of liquids. Water, for example has a dielectric constant approximately eighty times higher than that of air. Thus the presence of air bubbles in a liquid will cause a radical change in the dielectric loading of the microstrip with a resultant shift in the frequency of oscillation of the oscillator and the DC output of the discriminator. Depending on the size of the air bubble, frequency shifts from 1.0 Mhz to 100 Mhz have been observed in practice. As shown in FIG. 8, the existence of 100 mcl of air will result in a 40 Mhz frequency shift in the case of PVC tubing of a typical infusion administration set.

Referring again to FIG. 1, in the preferred embodiment, the signal processor 24 receives the electrical output signal 22 from the discriminator 18, which represents the oscillating frequency of the resonant stub 14. The processor 24 can make determinations based on changes to the oscillating frequency. The existence of a small amount of air in the fluid line segment 13 can be determined by comparing the frequency change to parameters that are either fixed, or "entered in" by the operator of a system which utilizes the in-line fluid monitor. The signal processor 24 includes conventional circuitry and programming for comparing the discriminator output voltage signal with a reference value and for determining the magnitude of perturbation of the oscillating frequency. The signal processor 24 is also preferably constituted so as to provide an output signal either to a display 26 and/or printer unit for viewing a real time graph of waveforms of the perturbation of oscillations and the signal processor may be adapted to simultaneously generate a signal to an alarm device 28, for indicating an alarm condition when the magnitude of perturbation is greater than a predetermined threshold value. The alarm device 28 may aurally indicate an alarm and may also be coupled to the pump controller 56 to automatically stop pump 58 operation.

Figure 10:
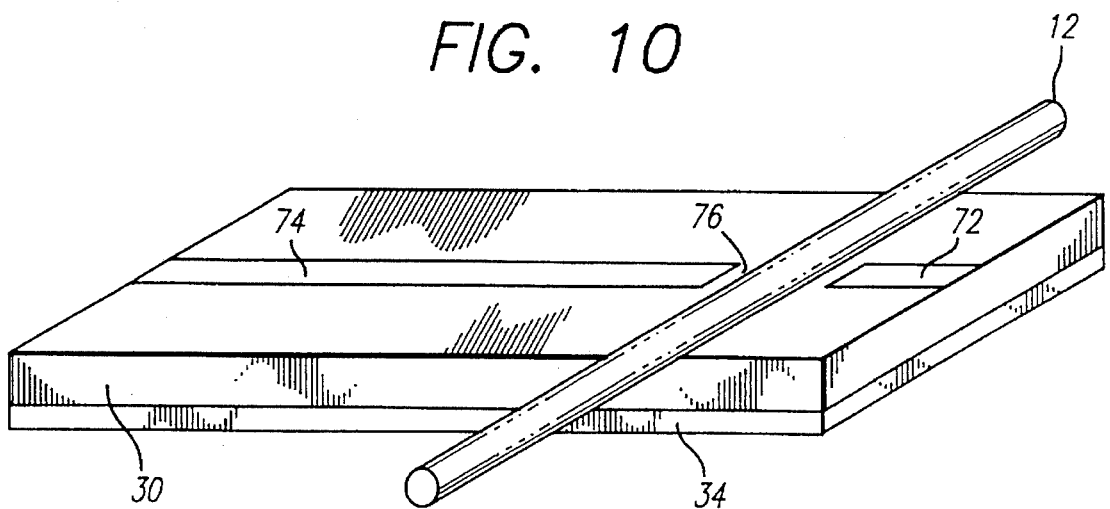
FIG. 10 is a detail view of the resonator of FIG. 9.
Figure 9:
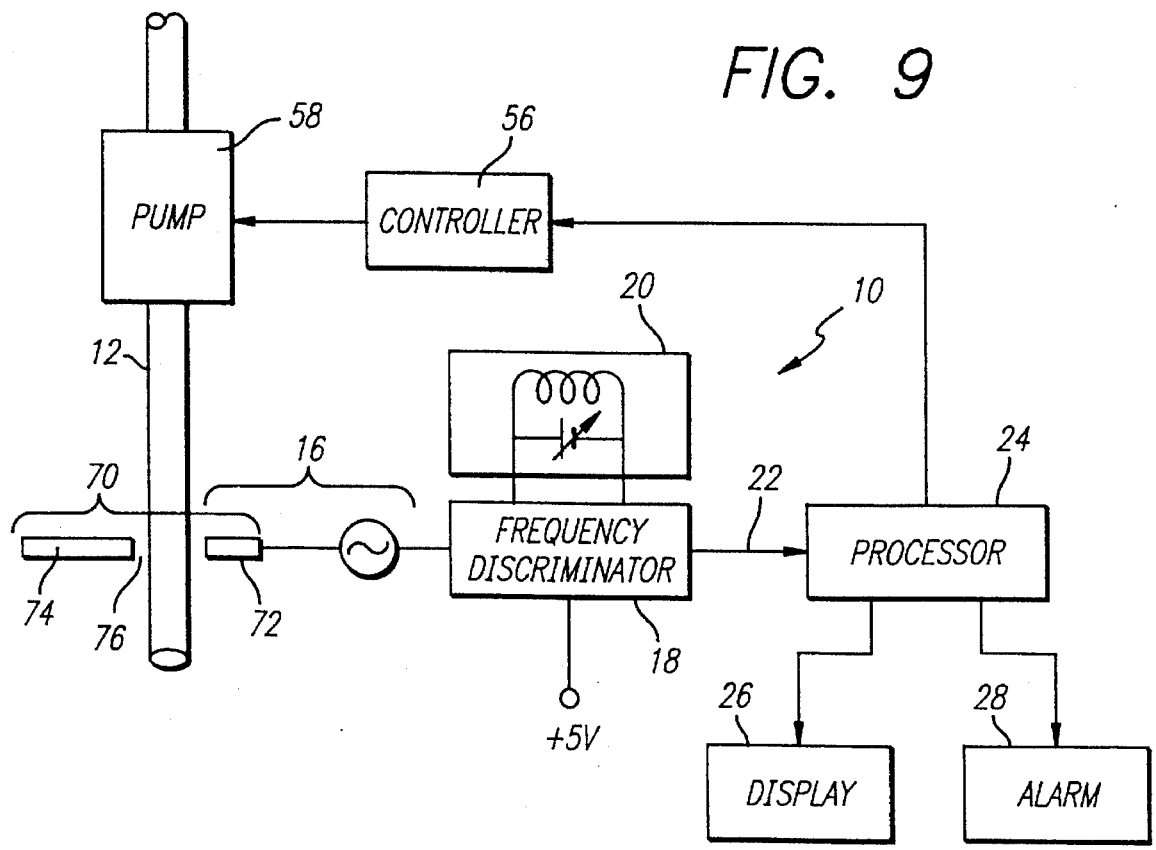
FIG. 9 is a block diagram wherein the resonator comprises a gap coupled microstrip structure.

Referring now to FIGS. 9 and 10, an alternate embodiment of an open resonator is illustrated. In this embodiment, gap coupling is used for the resonator 70 and the fluid tubing 12 is placed in the electric coupling field created by the gap. As shown, an input port 72, to which the oscillator 16 is connected is positioned on one side of the fluid tubing 12. The main stub 74 is positioned on the opposite side of the tubing. The input port 72 will couple to the main stub 74 across the gap 76 with a coupling electric field and that field will be affected by the fluid tubing 12 and its contents. The size of the gap 76 has been exaggerated in the FIGS. for clarity and would normally be smaller than that shown.

In forming the microstrip line for the embodiment shown in FIGS. 9 and 10, the width of the microstrip line can be selected to detect air bubbles of a certain size. However, the microstrip has a certain maximum width and if air bubbles larger than that width must be detected, a timing approach may be used as is discussed above. Additionally, while the fluid line is disposed in parallel with the gap 76 of the microstrip in FIGS. 9 and 10, it may be angled across the gap to expose somewhat more of the fluid line to the electric field created by the gap.

Although the open resonator shown in the drawings comprises a microstrip or stripline stub, other open resonators may be usable as well. For example, a cavity with an aperture through which the electric field protrudes outside the cavity may be used. The fluid tubing would be positioned to reside in that protruding electric field outside the cavity.

Figure 11:
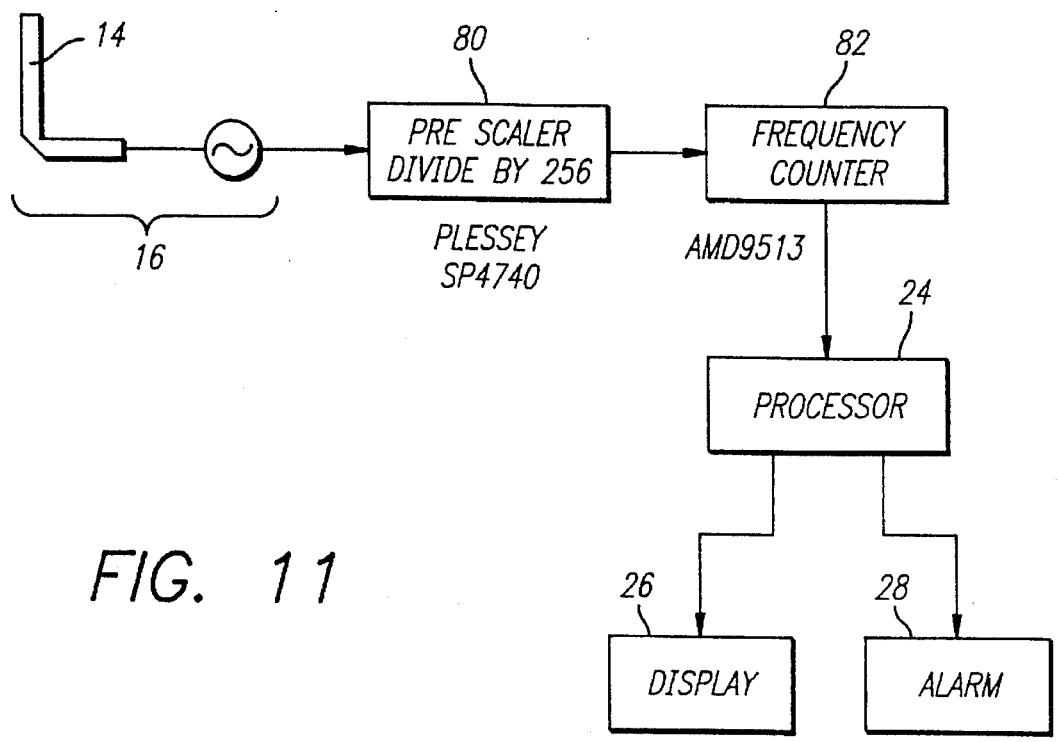
FIG. 11 is a block diagram of a detection system using a prescaler and a frequency counter to determine the frequency of oscillation of an oscillator connected to an open resonator.

Another embodiment is shown in FIG. 11 in which a prescaler 80 is used to divide the oscillator by a factor of 256 or higher, and a frequency counter 82 is used to provide a count to the processor 24. The prescaler and counter take the place of the frequency discriminator 18 of FIG. 1 and have been found to be particularly useful at relatively high frequencies. In one embodiment, a Plessey SP4740 was used for the prescaler and an AMD9513 was used as a frequency counter.

From the foregoing, it will be appreciated that the in-line fluid monitor system and method in accordance with the principles of the invention provides a simple, cost effective, and accurate way of detecting air in line. The fluid line may be disposable while the detection system 10 can be reused.

Although the system and method of the invention have been illustrated in terms of detecting air in a fluid line, other applications may be possible. Other substances besides air may be detected in various containers to which the resonator may be coupled. Additionally, although specific embodiments of the invention have been described and illustrated, it is clear that the invention is susceptible to numerous modifications and embodiments within the ability of those skilled in the art, and without the exercise of inventive faculty. Thus, it should be understood that various changes in form, detail and application of the present invention may be made without departing from the spirit and scope of the invention.

We claim:

1. A system for detecting the presence of a selected substance located in a container, the system comprising:

an open resonator having a selected characteristic that changes in response to the selected substance;

a circuit coupled to the open resonator that is responsive to the selected characteristic of the open resonator and that provides an output signal that varies in dependence on said selected characteristic of the open resonator;

a mounting structure arranged to mount the open resonator at a position outside the container and such that the existence of the selected substance in the container will change said characteristic of the open resonator; and a processor that receives the output signal of the circuit and determines the change in the output signal that is based on the change in the selected characteristic of the open resonator to detect the presence of the selected substance in the container.

2. The system of claim 1 wherein the output signal has a frequency and wherein the circuit is frequency dependent on the selected characteristic of the open resonator and varies the frequency of the output signal accordingly.

3. The system of claim 1 wherein:

the selected characteristic of the open resonator is its impedance;

wherein said impedance changes in response to the existence of the selected substance in the container; and, the circuit is responsive to the impedance of the open resonator and the output signal of the circuit varies in dependence on that impedance.

4. The system of claim 1 wherein the open resonator has a fringe electric field and the mounting structure is arranged to mount the open resonator such that the container is positioned in the fringe electric field of the open resonator.

5. The system of claim 4 wherein the mounting structure is arranged to position the container so that the entire fringe electric field of the open resonator includes at least part of the container.

6. The system of claim 1 wherein the main electric field and the mounting structure is arranged to mount the open resonator such that the container is positioned in the main electric field of the open resonator.

7. The system of claim 6 wherein the mounting structure is arranged to position the container so that the entire main electric field of the open resonator includes at least a part of the container.

8. The system of claim 1 wherein the open resonator comprises an elongated stub and the mounting structure mounts the elongate stub so that the fluid line segment is located in parallel with the elongated portion of the stub.

9. The system of claim 1 wherein:

a feed member is coupled to the open resonator by a gap disposed between them;

an electric field exists across the gap; and the mounting member is arranged to position the fluid line segment in the electric field across the gap.

10. A method for detecting the presence of a selected substance located in a container, the method comprising the steps of:

disposing an open planar resonator at a position outside the container such that the existence of the selected substance in the container will change a selected characteristic of the open resonator;

providing an output signal from a circuit coupled to the open resonator that is responsive to the selected characteristic of the open resonator such that the output signal varies in dependence on said characteristic of the open resonator; and processing the output signal of the circuit to determine the change in the output signal that is based on the change in the selected characteristic of the resonator to detect the presence of the selected substance in the container.

11. The method of claim 10 wherein:

the step of providing the output signal comprises the steps of providing the output signal with a frequency that varies in dependence on the selected characteristic of the open resonator; and the step of processing the output signal comprises the step of determining the change in frequency of the output signal to detect the presence of the selected substance in the container.

12. The method of claim 10 wherein:

the step of providing the, output signal comprises the step of circuit responding to the impedance of the open planar resonator and providing the output signal that varies in dependence upon the impedance of the open resonator;

the step of processing the output signal comprises the step of determining the change in the impedance of the open planar resonator indicated by the output signal to detect the presence of the selected substance in the container.

13. The method of claim 10 wherein the step of disposing open planar resonator comprises the step of positioning the open planar resonator in relation to the container so that the container is in a fringe electric field of the open resonator.

14. The method of claim 13 wherein the step of positioning the open planar resonator so that the container is in a fringe electric field comprises the step of positioning the open planar resonator so that the entire fringe electric field includes at least a part of the container.

15. The method of claim 10 wherein the step of disposing the open planar resonator comprises the step of positioning the open planar resonator so that the container is in a main electric field of the open resonator.

16. The method of claim 15 wherein the step of positioning the open planar resonator in the main electric field comprises the step of positioning the open planar resonator so that the entire main electric field includes at least a part of the container.

17. The method of claim 10 wherein the step of disposing the container comprises the step of disposing the container parallel to an open resonator that comprises an elongated stub with the container being located in parallel with the elongated portion of the stub.

18. The method of claim 10 wherein:

the step of disposing the open planar resonator further comprises the step of disposing a feed member in communication with the resonator so that a gap exists between them;

providing an electric field across the gap, and arranging the fluid line segment in the electric field across the gap.

19. A system for detecting the presence of a selected substance in fluid located in a fluid line segment, the system comprising:

an open planar resonator having a selected characteristic that changes in response to the selected substance;

a circuit coupled to the open resonator that is frequency dependent on the selected characteristic of the open resonator and that provides an output signal that varies in dependence on the frequency of the circuit;

a mounting structure arranged for mounting the open resonator at a position outside the container and such that the existence of the selected substance in the fluid line segment will change the characteristic of the open resonator; and a processor that receives the output signal of the circuit and determines the change in the frequency of the output signal that is based on the change in the selected characteristic of the open planar resonator to detect the presence of the selected substance in the fluid line segment.

20. The system of claim 19 wherein the open resonator comprises an elongated stub and the mounting structure mounts the open planar resonator and the elongated stub so that the fluid line segment is located in parallel with the elongated portion of the stub.

21. The system of claim 20 wherein the mounting structure mounts the elongated stub so that the fluid line segment is positioned between the stub and a ground plane such that the fluid line segment is located in a main electric field of the stub.

22. The system of claim 21 wherein the mounting structure mounts the elongated stub so that the fluid line segment is located such that the entire main electric field in which the fluid line segment is located includes at least a part of the fluid line segment.

23. The system of claim 20 wherein the length of the stub is equal to or greater than the maximum length of the selected substance permitted in the fluid line.

24. The system of claim 19 wherein:

the output signal has a frequency;

the processor comprises a prescaler that divides the output signal from the circuit by a predetermined divisor and counts the divided output signal to determine the frequency of the output signal;

the processor determines a change in the frequency of the output signal; and the processor compares the change in the frequency of the output signal to a threshold to determine a frequency change large enough to indicate the presence of an air bubble in the fluid line segment.

25. The system of claim 19 wherein:

a feed member is coupled to the open resonator by a gap, disposed between them;

an electric field exists across the gap; and the mounting member is arranged to position the fluid line segment in the electric field across the gap.

26. The system of claim 25 wherein the mounting member mounts the open planar resonator so that the fluid line segment is disposed parallel to the gap.

27. The system of claim 25 wherein the mounting member mounts the open planar resonator so that the fluid line segment is disposed at an angle other than parallel to the gap.

* * * * *

UNITED STATES PATENT AND TRADEMARK OFFICE
CERTIFICATE OF CORRECTION

PATENT NO.   : 5,455,565
DATED        : October 3, 1995
INVENTOR(S)  : Behzad Moeenziai, Kurt Zublin, Jack Goldberg It is certified that error appears in the above-indentified patent and that said Letters Patent is hereby corrected as shown below:

Claim 6, column 9, line 31, after "wherein the" add --open resonator has a--.

Claim 12, column 10, line 9, change "step" [second occurence] to --steps--.

column 10, line 10, add --the-- after of. (first occurence)

Signed and Sealed this

Thirtieth Day of July, 1996

Attest:

BRUCE LEHMAN

*Attesting Officer*  *Commissioner of Patents and Trademarks*